United States Patent [19]

James

[11] 4,060,611
[45] Nov. 29, 1977

[54] 3-CARBAMYLBENZYL-7-(PHENYLGLYCYL)-AMINO CEPHALOSPORIN DERIVATIVES

[75] Inventor: Brian George James, Cranleigh, England

[73] Assignee: Beecham Group Limited, Great Britain

[21] Appl. No.: 708,342

[22] Filed: July 26, 1976

[30] Foreign Application Priority Data

Aug. 15, 1975 United Kingdom .............. 34008/75

[51] Int. Cl.$^2$ ................... A61K 31/545; C07D 501/24
[52] U.S. Cl. ........................................ 424/246; 544/16
[58] Field of Search ..................... 260/243 C; 424/246

[56] References Cited

U.S. PATENT DOCUMENTS

| | | | |
|---|---|---|---|
| 3,222,363 | 12/1965 | Flynn | 260/243 C |
| 3,225,038 | 12/1965 | Flynn | 260/243 C |
| 3,270,009 | 8/1966 | Flynn | 260/243 C |
| 3,352,858 | 11/1967 | Crast et al. | 260/243 C |
| 3,971,778 | 7/1976 | Cook et al. | 260/243 C |
| 3,985,742 | 10/1976 | Stapley et al. | 260/243 C |

Primary Examiner—Nicholas S. Rizzo
Assistant Examiner—David E. Wheeler
Attorney, Agent, or Firm—Jacobs & Jacobs

[57] ABSTRACT

Antibacterial 3-carbamoylbenzyl cephems and 3-(carbamoylpyridylmethyl) cephems, pharmaceutically acceptable salts and in vivo hydrolyzable esters thereof; pharmaceutical compositions containing antibacterially effective amounts of such cephems and intermediates therefor. Minimum inhibitory concentrations against various bacteria are given. The cephems and compositions containing the same are suitable for administration in conventional forms to humans.

15 Claims, No Drawings

3-CARBAMYLBENZYL-7-(PHENYLGLYCYL)-AMINO CEPHALOSPORIN DERIVATIVES

This invention relates to antibacterial 3-carbamoylbenzyl cephems and 3-(carbamoylpyridylmethyl)cephems.

United States Application Ser. No. 562,547 and United Kingdom Application No. 15805/74 disclose compounds of the formula (I):

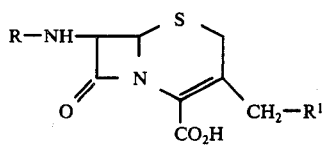

and their salts and in-vivo hydrolysable esters wherein R is an acyl group as found in known antibacterially active penicillins and cephalosporins and $R^1$ is a mono- or di- carboxyphenyl group. Such compounds were shown to possess useful antibacterial activity.

Belgian Patent No. 809961 disclosed inter alia compounds of the formula (I) and their salts and in-vivo hydrolysable esters wherein R is an acyl group as found in known antibacterially active penicillins and cephalosporins and $R^1$ is a pyridyl group. Such compounds were also shown to possess useful antibacterial activity.

We have now found a class of cephems which possess improved antibacterial activity.

Accordingly the present invention provides compounds of the formula (II):

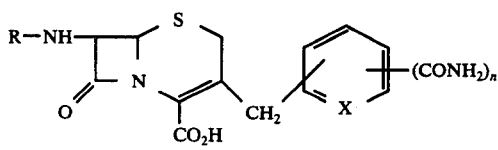

wherein R is an acyl group as in reported natural and semi-synthetic antibacterially active penicillins and cephalosporins; X is CH or N; and n is 1 or 2; and pharmaceutically acceptable salts and in-vivo hydrolysable esters thereof.

Belgian Patent No. 809961 should be consulted for suitable definitions of 'acyl group in reported natural and semi-synthetic antibacterially active penicillins and cephalosporins', 'salts' and 'in-vivo hydrolysable esters'.

In a particularly suitable aspect the present invention provides compounds of the formula (III):

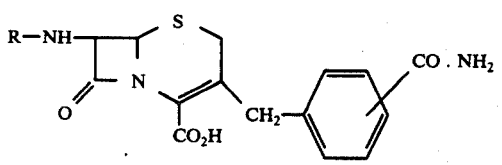

and pharmaceutically acceptable salts and in-vivo hydrolysable esters thereof wherein R is as defined in relation to formula (II).

Most suitably the compound of the formula (III) contains a free or salted carboxyl group at the 4- position of the cephem system.

Particularly suitable groups R for inclusion in compounds of the formulae (II) and (III) include those of the sub-formula (a):

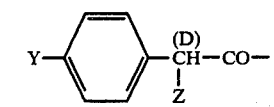

wherein Y is H or OH and Z is $NH_2$ or OH. Most suitably Z is $NH_2$.

In another aspect the present invention also provides pharmaceutical compositions which contain a compound of the formula (II) as hereinbefore defined. Such compositions will be adapted for administration to humans in a manner conventional for cephalosporins.

In a further aspect the present invention provides a process for the preparation of compounds of the formula (II) and salts thereof which process comprises the deprotection of the 4- carboxyl function of a molecule of the formula (IV):

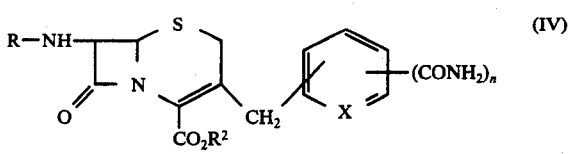

wherein R, X and n are as defined in relationship to formula (II) and $CO_2R^2$ is an ester group Suitable groups $CO_2R^2$ include those which may be converted by hydrolysis or hydrogenolysis to a free or salted carboxyl group under reaction conditions which do not lead to the destruction of the cephem system.

Suitable groups $CO_2R^2$ which may be converted to free or salted carboxyl groups by acid include t-butyl, benzhydryl, dimethoxybenzhydryl, trityl and chemically equivalent groups.

Suitable groups $CO_2R^2$ which may be converted to free or salted carboxyl groups by hydrogenolysis include benzyl, methoxybenzyl, benzhydryl, dimethoxybenzhydryl and chemically equivalent groups.

A particularly suitable group $CO_2R^2$ is the $CO_2C(CH_3)_3$ group.

If desired reactive substituents present in the group R may be reversibly protected during the synthesis of the compounds of formula (II). In such cases it is frequently convenient to select protecting groups which may be removed at the same time as removing the protecting group from the $CO_2R^2$ group. Thus, for example, amine groups may be protected as $NH.CO.OCH_2Ph$, $NH.CO.O.C(CH_3)_3$ or the like.

Suitable reaction conditions for removal of the protecting groups are similar to those desired in the aforesaid Belgian Patent and British and U.S. Patent Applications.

The compounds of formula (IV) are useful intermediates and as such form as important aspect of this invention.

Esters of the compounds of formula (II) may be prepared by the reaction of ammonia and a compound of the formula (V):

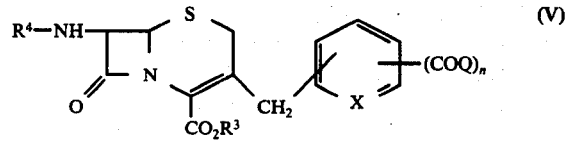

wherein Q is a chlorine or bromine atom and $R^4$ is a group $R^2$ in which any reactive group is reversibly protected in conventional manner, and $Co_2R^3$ is an ester group $CO_2R^2$ or $CO_2R^5$ where $CO_2R^2$ is as defined in relation to formula (IV) and $CO_2R^5$ is an in-vivo hydrolysable ester group.

The preceding reaction is generally carried out in an inert solvent such as dry tetrahydrofuran, dry dioxane or the like at a nonextreme temperature, for example, 0° C - 25° C.

The acid halides of the formula (V) may be prepared from the corresponding acids by reaction with thionyl chloride or thionyl bromide in conventional manner; for example, the reaction may be carried out in an inert solvent at a non-extreme temperature.

It is frequently convenient to prepare the acid halide of the formula (V) in situ and immediately react it with ammonia.

The following Examples illustrate the present invention:

EXAMPLE 1

3-(p-Carbamoylbenzyl)-7β-(D-α-phenylglycyl)amino-ceph-3-em-4-carboxylic acid (6)

a. Preparation of t-Butyl 7β-amino-3-(p-carboxybenzyl)ceph-3-em-4-carboxylate (2)

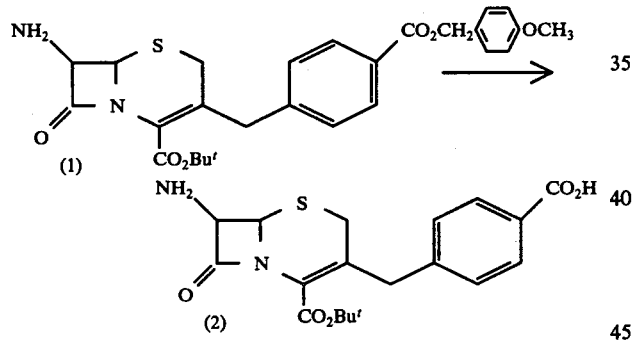

A solution of the amino ester (1) (2.0 g) in toluene (40 ml) was cooled (0° to 5°) in an ice-bath. Trifluoroacetic acid (4 ml) was added and the orange coloured solution stirred for a further 2.5 hrs at 0°–5°. The mixture was evaporated to dryness and re-evaporated twice from toluene. Trituration of the residue with ether gave the acid (2) as the trifluoroacetic acid salt (1.39 g), $\nu_{max}$ (KBr) 1780, 1690 (br) cm$^{-1}$; δ ppm [(CD$_3$)$_2$SO] 1.58 (s, 9H), 3.5 (bs, 2H), 3.75 and 4.22 (ABq, 2H, J=14 Hz), 5.0–5.35 (m, 2H), 7.52 (d, 2H, J=9 Hz), 8.24 (d, 2H, J=9 Hz), 9.1 (bs, 3H, exch. D$_2$O).

b. Preparation of t-Butyl 3-(p-carboxylbenzyl)-7β-(N-t-butoxycarbonyl-D-α-phenylglycyl)amino-ceph-3-em-4-carboxylate (4)

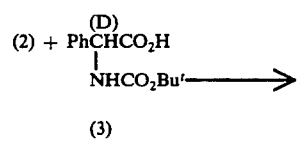

Triethylamine (166 mg), N-(t-butoxycarbonyl)-D-α-phenylglycine (412 mg) and N,N-dimethylbenzylamine (1 drop) in dry tetrahydrofuran (10 ml) was added dropwise to a solution of methylchloroformate (152 mg) in tetrahydrofuran (2 ml) cooled to −20°. This reaction mixture was stirred at −20° for 0.5 hrs., when a solution of the trifluoroacetic acid salt of (2) (680 mg) in tetrahydrofuran (10ml) containing triethylamine (166 mg) and dimethylformamide (3 drops) was added dropwise over 10 minutes. After stirring for 2 hours at −20° the reaction mixture was diluted with ethyl acetate and washed with water. Evaporation of the dried ethyl acetate layer, followed by trituration with a mixture of ether-petroleum ether gave the acid (4) (550 mg), $\nu_{max}$ 3350, 1780, 1710, 1690 cm$^{-1}$; δ ppm [(CD$_3$)$_2$SO] 1.4 (s, 9H), 1.52 (s, 9H), 2.9–4.2 (m, 4H), 5.0 (m, 1H), 5.35 (m, 1H), 5.75–6.0 (m, 2H), 7.2–7.7 (m, 9H), 8.0–8.35 (m, 2H).

c. Preparation of t-Butyl 3-(p-carbamoylbenzyl)-7β-(N-t-butoxycarbonyl-D-α-phenylglycyl)amino-ceph-3-em-4-carboxylate (5)

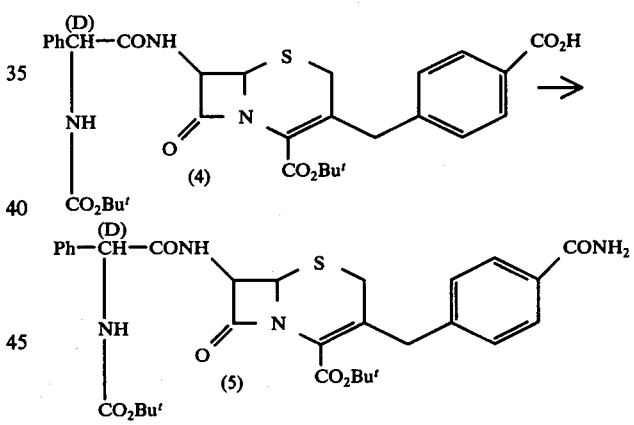

A solution of the acid (4) (300 mg) in dry tetrahydrofuran (5 ml) containing DMF (3 drops) was treated with thionyl chloride (360 mg). After 0.5 hrs at room temperature a solution of ammonia gas in tetrahydrofuran was added dropwise until the reaction mixture remained basic. The solution was diluted with ethyl acetate and washed with water. The dried ethyl acetate layer was evaporated and the residue chromatographed on silica gel to give the amide (5) (174 mg) as an amorphous solid, $\nu_{max}$ 3350, 1780, 1710, 1680 cm$^{-1}$; δ ppm (CDCl$_3$) 1.42 (s, 9H), 1.52 (s, 9H), 2.9–3.4 (m, 2H), 4.03 (m, 2H), 5.0 (d, 1H, J=5 Hz), 5.42 (d, 1H, J=8 Hz), 5.7–6.0 (m, 2H), 6.1–6.5 (m, 1H), 7.2–7.9 (m, 11H).

d. Preparation of 3-(p-Carbamoylbenzyl)-7β-(D-α-phenylglycyl)amino-ceph-3-em-4-carboxylic acid (6)

(5)⟶

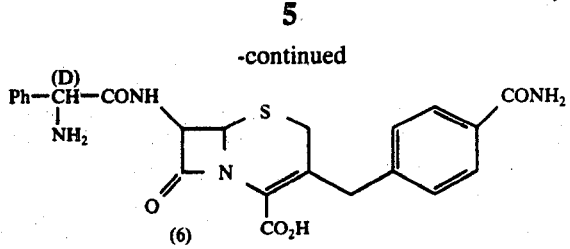

A solution of the amide (5) (87 mg) in trifluoroacetic acid (3 ml) was left at room temperature for 10 minutes. The trifluoroacetic acid was removed in vacuo and the residue re-evaporated from toluene. Trituration of the residue with ether gave the acid (6) (66 mg) as the trifluoroacetic acid salt, $\nu_{max}$ (KBr) 1770, 1675 (br) cm$^{-1}$.

The minimum inhibitory concentrations (MIC) of this compound required to inhibit the growth of various bacteria on nutrient agar are tabulated below:-

| Gram-positive bacteria | MIC (µg/ml) |
| --- | --- |
| B. subtilis | 0.1 |
| Staph. aureus Oxford | 0.1 |
| Staph. aureus Russell | 2.5 |
| β-haemolytic strep. CN10 | 0.01 |
| Gram-negative bacteria | |
| E. coli JT1 | 2.5 |
| Salm. typhi | 2.5 |
| Shig. sonnei | 2.5 |
| Klebsiella aerogenes A | 1.0 |
| P. mirabilis 889 | 2.5 |

EXAMPLE 2

3-(p-Carbamoylbenzyl)-7β-(D-α-p-hydroxyphenylglycyl)amino-ceph-3-em-4-carboxylic acid (10)

a. Preparation of t-Butyl 3-(p-carboxybenzyl)-7β-(N-t-butoxycarbonyl-D-α-p-hydroxyphenylglycyl)amino-ceph-3-em-4-carboxylate (8)

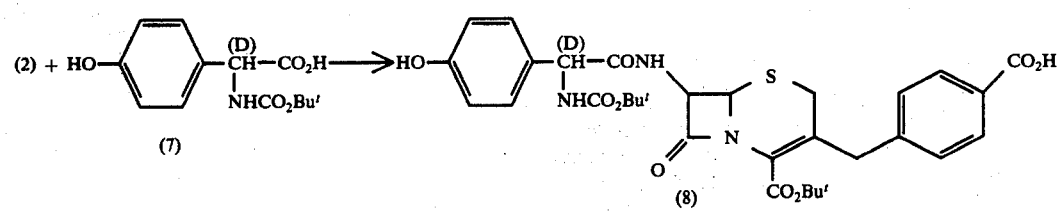

The amino-acid (2) (250 mg of trifluoroacetic acid salt) in tetrahydrofuran (5 ml) containing triethylamine (83 mg) and DMF (3 drops-was treated with the mixed anhydride prepared from N-(t-butoxycarbonyl)-D-α-p-hydroxyphenylglycine (0.23 g) and methyl chloroformate (73 mg) as in example (1 b). The acid (8) (244 mg) was an amorphous solid, $\nu_{max}$ 3500, 3350, 1780, 1710, 1690 cm$^{-1}$; δ ppm [(CD$_3$)$_2$SO] 1.40 (s, 9H), 1.52 (s, 9H), 2.9–4.2 (m, 5H), 4.9–5.4 (m, 2H), 5.7–6.0 (m, 2H), 6.7–7.7 (m, 8H), 7.9–8.3 (m, 2H).

b. Preparation of t-Butyl 3-(p-carbamoylbenzyl)-7β-(N-butoxycarbonyl-D-α-p-hydroxyphenylglycyl)amino-ceph-3-em-4-carboxylate (9)

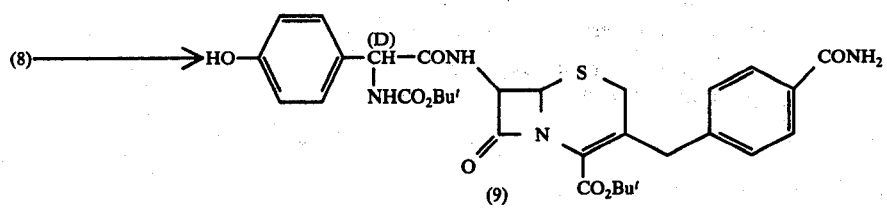

The acid (8, 224 mg) was treated with thionylchloride (68 mg) followed by ammonia as in example (1 c). Work up and chromatography gave the amide (9) (110 mg) as a solid, $\nu_{max}$ 3500, 3350, 1780, 1710, 1680 cm$^{-1}$; δ ppm (CDCl$_3$) 1.38 (s, 9H), 2.9–3.5 (m, 2H), 4.0–4.4 (m, 2H), 4.95 (d, 1H, J=5Hz), 5.25 (m, 1H), 5.7–6.2 (m, 2H), 6.6–6.9 (m, 2H), 7.1–7.9 (m, 9H).

c. Preparation of 3-(p-Carbamoylbenzyl)-7β-(Dα-p-hydroxyphenylglycyl) amino-ceph-3-em-4-carboxylic acid (10)

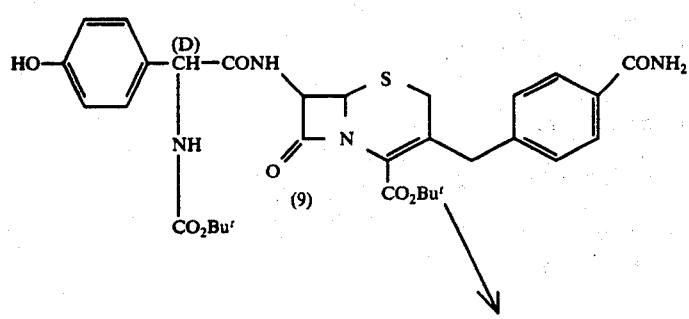

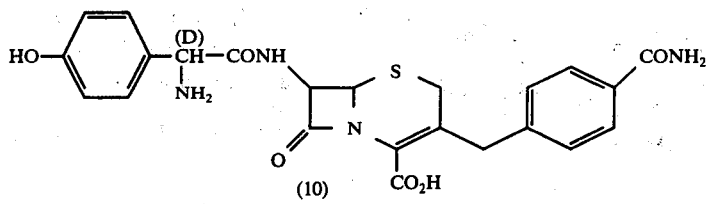

The amide (9) (100 mg) was treated with trifluoroacetic acid (2 ml) for 15 minutes at room temperature and worked up as in (1 d) to give the trifluoroacetic acid salt of (10) (60 mg), $\nu_{max}$(KBr) 1770, 1675 (br) cm$^{-1}$.

The minimum inhibitory concentrations (MIC) of this compound required to inhibit the growth of various bacteria on nutrient agar are tabulated below:

| Gram-positive bacteria | MIC (μg/ml) |
|---|---|
| B. Subtilis | 0.25 |
| Staph. aureus Oxford | 0.1 |
| Staph aureus Russell | 1.0 |
| β-haemolytic Strep. CN10 | 0.02 |
| Gram-negative bacteria | |
| E. coli JT1 | 2.5 |
| Salm. typhi | 0.5 |
| Shig. sonnei | 2.5 |
| Klebsiella aerogenes A | 1.0 |
| P. mirabilis C 977 | 2.5 |
| P. mirabilis 899 | 5.0 |

EXAMPLE 3

3-(p-Carbamoylbenzyl)-7β-(DL-α-phenoxycarbonyl-phenylacetamido)ceph-3-em-4-carboxylic acid (14)

a. Preparation of t-Butyl 3-(p-carboxybenzyl)-7β-(DL-α-phenoxycarbonylphenylacetamido)ceph-3-em-4-carboxylate (12)

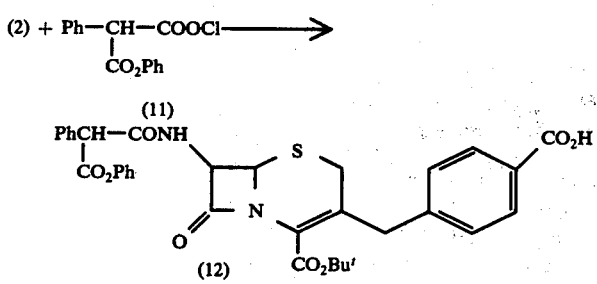

A solution of the cephem (2) (240 mg) is methylene chloride (5ml) at −10° was treated with triethylamine (140 mg) followed by the acid chloride (11) (200 mg) in methylene chloride. The reaction mixture was stirred at −10° for 0.5 hrs, then washed with water and dried. Evaporation of the methylene chloride and trituration of the residue with ether gave the acid (12) as a solid, δ ppm (CDCl$_3$) 1.48 (s, 9H), 2.9–3.7 (m, 3H), 3.95–4.2 (m, 1H), 4.92 (s, 1H), 5.1 (d, 1H, J=5 Hz), 5.8–6.18 (m, 1H), 7.0–8.3 (m, 16H).

b. Preparation of t-Butyl-3-(p-carbamoylbenzyl)-7β-(DL-α-phenoxycarbonylphenylacetamido)ceph-3-em-carboxylate (13)

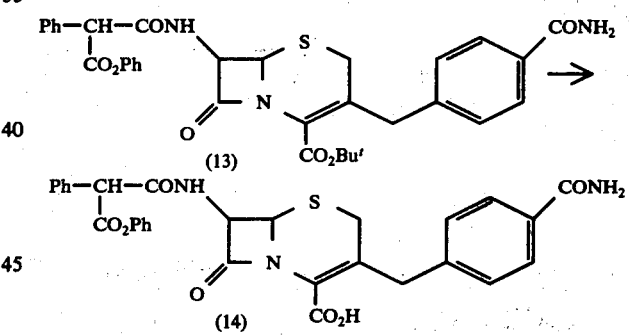

A solution of the acid (12) (90mg) in tetrahydrofuran (5ml) was treated with thionyl chloride (68mg) at room temperature. The mixture was stirred for 0–5 hours, when a solution of ammonia gas in tetrahydrofuran was added dropwise until the reaction remained basic. The solution was diluted with ethyl acetate and washed with water. Evaporation of the dried solution gave a residue which was chromatographed to give the amide (13) (54mg) as a solid, $\nu$max 3350, 1780, 1710, 1680 (br)cm$^{-1}$; δ ppm (CDCl$_3$) 1.58 (s, 9H), 3.0 – 3.6 (m, 3H), 4.20 (d, 1H, J=15Hz half of ABq), 4.98 – 5.1 (m, 2H), 5.7 – 6.0 (m, 1H), 6.1 – 6.9 (m, 1H, 7.0 – 8.0 (m, 16H).

c. Preparation of 3-(p-Carbamoylbenzyl)-7β-(DL-α-phenoxycarbonylphenylacetamido)ceph-3-em-4-carboxylic acid (14)

The cephem (13) (50 mg) was treated with trifluoroacetic acid (3 ml) for 15 minutes at room temperature as in example (2 c) to give the acid (14) (33 mg) as a solid, $\nu_{max}$(KBr) 1780 cm$^{-1}$.

The minimum inhibitory concentrations (MIC) of this compound required to inhibit the growth of various bacteria on nutrient agar are tabulated below:

| Gram-positive bacteria | MIC (μg/ml) |
|---|---|
| B. subtilis | 10 |
| Staph. aureus Oxford | 1.0 |
| Staph. aureus Russell | 10 |
| β-haemolytic Strep. CN10 | 1.0 |
| Gram-negative bacteria | |
| E. coli JT1 | 5.0 |
| Salm. typhi | 10 |
| Shig. sonnei | 5.0 |
| Klebsiella aerogenes A | 10 |
| Enterobacter cloacae N1 | 10 |
| P. mirabilis C977 | 5.0 |
| P. rettgeri | 5.0 |

EXAMPLE 4

3-(m-Carbamoylbenzyl)-7β-(D-α-phenylglycyl)amino-ceph-3-em-4-carboxylic acid (19) a. Preparation of t-Butyl 7β-amino-3-(m-carboxylbenzyl)ceph-3-em-4-carboxylate (16)

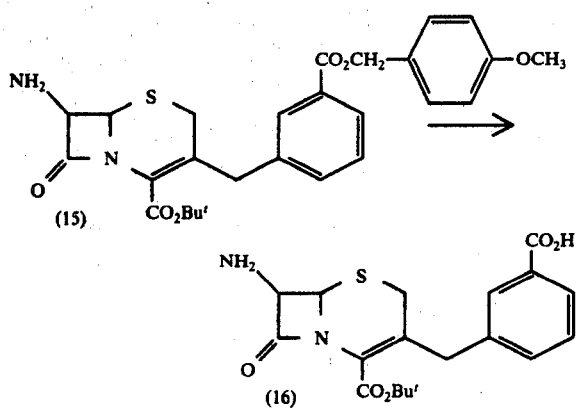

A solution of the cephem (15) (511 mg) in toluene (20 ml) was cooled (ice-bath) and treated with trifluoroacetic acid (1 ml). After standing for 2 hours at 0° to 5° the reaction was left overnight at −10° and then treated with a further 1 ml of trifluoroacetic acid. The reaction was worked up as in example (1a) after keeping for a further 5 hours at −10°. The product (16) (437 mg) was obtained as the trifluoroacetic acid salt, $\nu_{max}$(KBr) 1780, 1720–1670 cm$^{-1}$.

b. Preparation of t-Butyl 3-(m-carboxybenzyl)-7β-(N-t-butoxycarbonyl-D-α-phenylglycyl)amino-ceph-3-em-4-carboxylate (17)

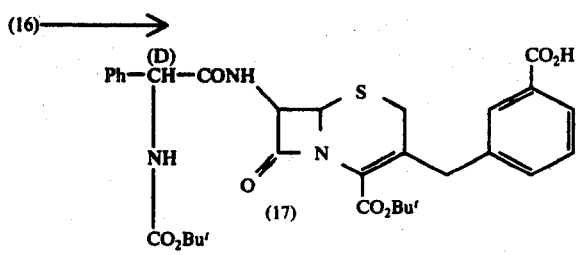

The trifluoroacetic acid salt of (16) (274 mg) and triethylamine (55 mg) in tetrahydrofuran (10 ml) was treated with the mixed anhydride of N-(t-butoxycarbonyl)-D-α-phenylglycine as in example (1b). The product (17) was a solid (233 mg), $\nu_{max}$ (CHCl$_3$) 3400, 1780, 1718–1685 cm$^{-1}$; δ ppm (CDCl$_3$) 1.40 (s, 9H), 1.53 (s, 9H), 3.10–4.30 (m, 4H), 5.0 (d, 1H, J=5 Hz), 5.20–5.47 (m, 1H), 5.68–6.03 (2H, 1H exch. D$_2$O), 5.77–8.23 (11H, 1H exch. D$_2$O).

c. Preparation of t-Butyl 3-(m-carbamoylbenzyl)-7β-(N-t-butoxycarbonyl-D-α-phenylglycyl)amino-ceph-3-em-4-carboxylate (18)

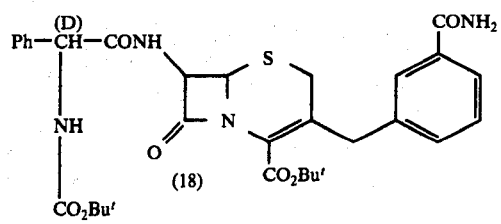

A solution of the acid (17) (143 mg) in dry tetrahydrofuran (20 ml) was treated with thionyl chloride (136 mg) and dimethylformamide (4 drops), followed by ammonia as in example (1c). Work up and chromatography gave the amide (18) as a white solid, $\nu_{max}$ (CHCl$_3$) 3400, 1780, 1710, 1680, cm$^{-1}$; $\lambda_{max}$ (Ethanol) 267 nm (ε9,630); δ ppm (CDCl$_3$) 1.43 (s, 9H), 1.57 (s, 9H), 2.80–3.90 (m, 4H), 5.0 (d, 1H, J=5 Hz), 5.30–5.48 (m, 1H), 5.72–5.99 (m, 2H), 6.19–6.60 (2H, 1H exch. D$_2$O), 7.20–8.10 (10 H).

d. 3-(m-Carbamoylbenzyl)-7β-phenylglycyl)amino-ceph-3-em-4-carboxylic acid (19)

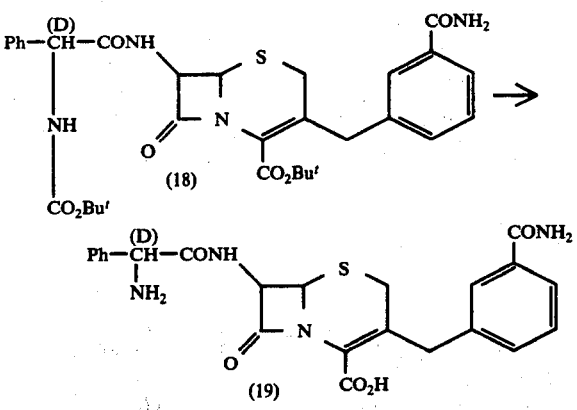

A solution of the cephem (18) (23 mg) in trifluoroacetic acid (1 ml) was left at room temperature for 20 minutes. The product (19) was isolated as in example (1d) and obtained as the trifluoroacetic acid salt, $\nu_{max}$ (KBr) 1768, 1660 cm$^{-1}$, $\lambda_{max}$ (Ethanol) 266 nm (ε9,380).

The minimum inhibitory concentrations (MIC) of this compound required to inhibit the growth of various bacteria on nutrient agar are given below:

| Gram-positive bacteria | MIC (μg/ml) |
|---|---|
| B. subtilis | 0.1 |
| Staph. aureus Oxford | 0.1 |
| Staph. aureus Russell | 2.5 |
| β-haemolytic Strep. CN10 | 0.05 |
| Gram-negative bacteria | |
| Salm. typhi | 10 |
| Klebsiella aerogenes A | 5.0 |
| P. mirabilis 889 | 10 |

EXAMPLE 5

3-(3,5-dicarbamoylbenzyl)-7β-(D-α-phenylglycyl)amino-ceph-3-em-4-carboxylic acid (24)

a. Preparation of t-Butyl 7β-amino-3-(3,5-dicarboxybenzyl)ceph-3-em-4-carboxylate (21)

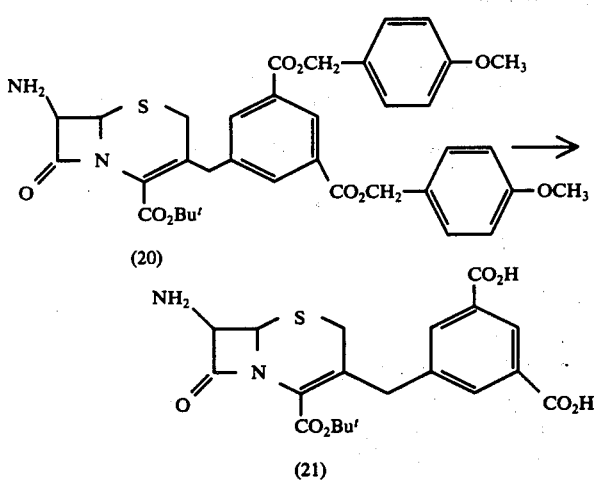

(20)

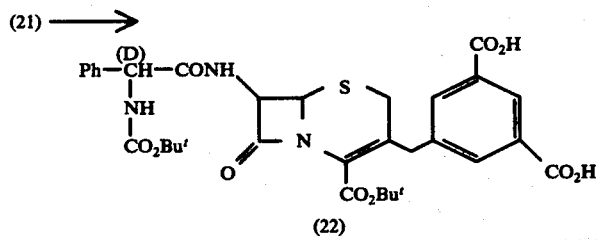

(21)

A solution of the amino ester (20) (675 mg) in toluene (20 ml) was cooled (ice-bath) and treated with trifluoroacetic acid (2 ml). The reaction was stirred at 0° to 5° for 2 hours and then kept at −10° overnight. Work up as in example (1a) gave the amino-acid (21) (340 mg) as the trifluoroacetic acid salt, $\nu_{max}$ (KBr) 1775, 1700 (b) cm$^{-1}$; δ ppm [(CD$_3$)$_2$SO] 1.52 (s, 9H), 3.30–4.06 (m, 4H), 5.27 (broad signal giving on D$_2$O exchanged δ 5.22 (d) and 5.37 (d), 2H, J=5 Hz), 8.27 (s, 2H), 8.50 (s, 1H), 7.8–10 (bs, exch, with D$_2$O 5H).

b. Preparation of t-Butyl 3-(3,5-dicarboxybenzyl)-7β-(N-t-butoxycarbonyl-D-α-phenylglycyl)amino-ceph-3-em-4-carboxylate (22)

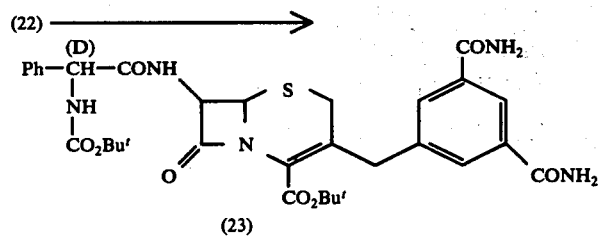

(22)

The mixed anhydride from N-(t-butoxycarbonyl)-D-α-phenylglycine(150 mg), triethylamine (61 mg) N,N-dimethylbenzylamine (1 drop) and methylchloroformate (57 mg) was reacted with the trifluoroacetic acid salt of (21) (298 mg) and triethylamine (55 mg) as in example (1 b). The cephem (22) (366 mg) was an amorphous solid, $\nu_{max}$ (CHCl$_3$) 1785, 1715 (b) cm$^{-1}$.

c. Preparation of t-Butyl 3-(3,5-dicarbamoylbenzyl)-7β-(N-t-butoxycarbonyl-D-α-phenylglycyl)amino-ceph-3-em-4-carboxylate (23)

(22) ⟶

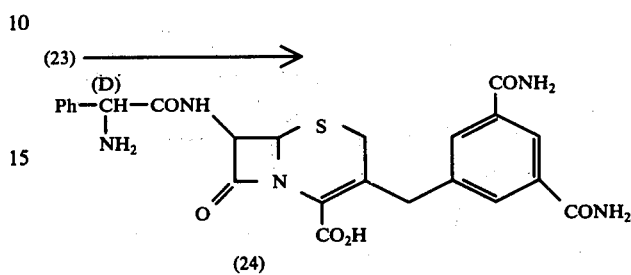

(23)

The acid (22) (218 mg) in dry tetrahydrofuran (40 ml) was treated with thionyl chloride (388 mg) and dimethylformamide (10 drops). After 45 minutes the solution was neutralised by the addition of a solution of ammonia in tetrahydrofuran. The mixture was stirred for a further 30 minutes, worked up and chromatographed as in (1 c) to give the amide (23) (40 mg) as a solid m.p. >210° (d), $\nu_{max}$(KBr) 1775, 1720–1650 cm$^{-1}$; $\lambda_{max}$(ethanol) 267 nm ($\epsilon$ 11,300).

d. Preparation of 3-(3,5-dicarbamoylbenzyl)-7β-(D-α-phenylglycyl)amino-ceph-3-em-4-carboxylic acid (24)

(23) ⟶

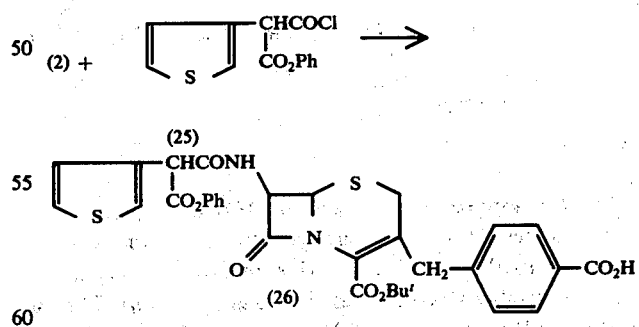

(24)

The protected cephem (23) (20 mg) in trifluoroacetic acid (0.5 ml) was left at room temperature for 30 minutes. Isolation as in (1 d) gave the trifluoroacetic acid salt of (24), $\nu_{max}$ (KBr) 1765, 1660 cm$^{-1}$; $\lambda_{max}$ (ethanol) 266 nm ($\epsilon$ 5,900).

The minimum inhibitory concentrations (MIC) of this compound required to inhibit the growth of various bacteria on nutrient agar are tabulated below:

| Gram-positive bacteria | MIC (μg/ml) |
|---|---|
| B. subtilis | 2.5 |
| Staph. aureus Oxford | 0.5 |
| Staph. aureus Russell | 5.0 |
| β-haemolytic Strep. CN10 | 0.5 |
| Gram-negative bacteria | |
| Salm. typhi | 10 |
| Shig sonnei | 10 |
| Klebsiella aerogenes A | 5.0 |

EXAMPLE 6

3-(p-Carbamoylbenzyl)-7β-(DL-α-phenoxycarbonyl-3¹-thienylacetamido)ceph-3-em-4-carboxylic acid a. Preparation of t-Butyl-3-(p-carboxylbenzyl)-7β-(DL-α-phenoxycarbonyl-3¹-thienylacetamido)ceph-3-em-4-carboxylate (26)

A solution of the cephem (2) (756 mg) in dichloromethane (10 ml) was cooled to −10° and treated with triethylamine (606 mg) followed by the acid chloride (533 mg) in dichloromethane. The reaction mixture was stirred at −10° for 1 h then diluted with dichloromethane and washed with dilute hydrochloric acid and water. The dried (MgSO$_4$) organic phase was evaporated and the residue triturated with ether/pet. ether to give the acid (26) (717 mg) as a solid.

b. Preparation of t-Butyl-3-(p-carbamoylbenzyl)-7β-(DL-α-phenoxylcarbonyl-3¹-thienylacetamido)ceph-3-em-4-carboxylate (27)

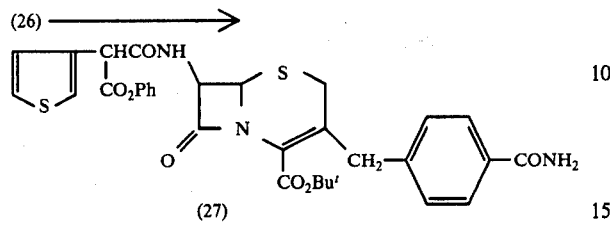

A solution of the crude acid (26) (649 mg) in tetrahydrofuran (50 ml) containing dimethylformamide (2 drops) was treated with thionyl chloride (244 mg) at room temperature. The mixture was stirred for 1 h, when a solution of ammonia gas in tetrahydrofuran was added dropwise until the reaction remained basic. The solution was diluted with ethyl acetate and washed with water. Evaporation of the dried organic phase gave a residue which was chromatographed to give the amide (27) (162 mg) as a solid. $\nu_{max}$(CHCl₃) 3350, 1765, 1700, 1665 cm⁻¹. δ ppm (CDCl₃) 1.51 (s, 9H), 2.98 and 3.34 (ABq, 2H, J = 18 Hz), 3.41 and 4.12 (ABq, 2H, J = 15 Hz), 4.9–5.05 (m, 2H), 5.6–6.1 (broad m, 3H), 6.9–7.9 (m, 13H).

c. Preparation of 3-(p-Carbamoylbenzyl)-7β-(DL-α-phenoxycarbonyl-3¹-thienylacetamido)ceph-3-em-4-carboxylic acid (28)

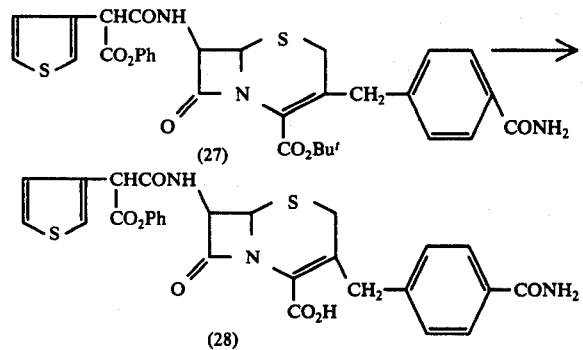

The cephem (27) (135 mg) was treated with trifluoroacetic acid (3 ml) for 10 min at room temperature. The reaction mixture was evaporated to an oil, then reevaporated twice from toluene. Trituration of the residue with ether gave the acid (28) (97 mg) as a solid.

The minimum inhibitory concentrations (MIC) of this compound against various bacteria are tabulated below:

|  | MIC (μg/ml) |
| --- | --- |
| B. subtilis | 25 |
| Staph. aureus Oxford | 12.5 |
| Staph. aureus Russell | 25 |
| β-haemolytic Strep. CN10 | 25 |
| E. coli JT1 | 5.0 |
| Klebsiella aerogenes A | 2.5 |
| Enterobacter cloacae N1 | 12.5 |
| P. mirabilis C977 | 12.5 |
| P. rettgeri | 5.0 |

EXAMPLE 7

Preparation of 3-(p-Carbamoylbenzyl)-7β-[D-α-(3-cinnamoyl-3-methyluriedo)phenylacetamido]ceph-3-em-4-carboxylic acid

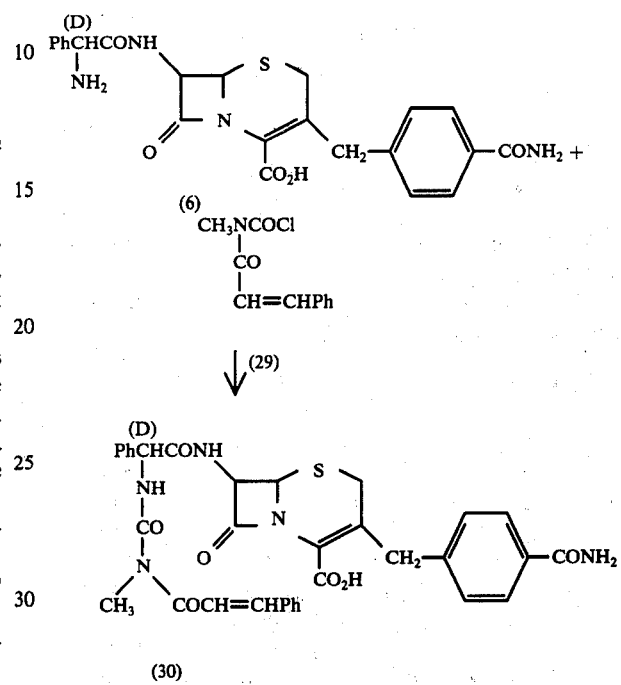

The cephem (6) as the trifluoroacetic acid salt (353 mg) in dichloromethane was cooled to 0° – 5° and treated with triethylamine (184 mg) followed by the carbamoyl chloride (29) (149 mg). The mixture was stirred at room temperature for 3 h when it was evaporated to dryness and the residue partitioned betweem ethylacetate and water. The pH was adjusted to 2 and the system separated. The organic phase was washed with water, dried (MgSO₄) and evaporated to a gum which solidified on trituration with ether, to give compound (30) (120 mg) $\nu_{max}$ (nujol): 1763, 1670 (br) cm⁻¹.

The minimum inhibitory concentrations (MIC) of the compound against various bacteria are tabulated below:

|  | MIC (μg/ml) |
| --- | --- |
| B. subtilis | 5.0 |
| Staph. aureus Oxford | 0.1 |
| Staph. aureus Russell | 12.5 |
| β-Haemolytic Strep. CN10 | 0.05 |
| E. coli JT1 | 5.0 |
| Klebsiella aerogenes A | 5.0 |
| P. mirabilis C977 | 5.0 |
| P. rettgeri | 12.5 |
| P. morganii | 5.0 |

What is claimed is:

1. A compound of the formula:

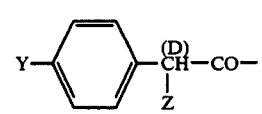

15

-continued

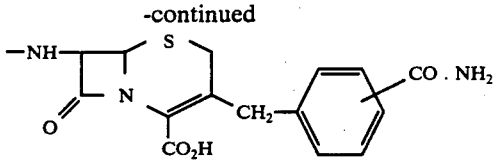

pharmaceutically acceptable salt thereof wherein Y is H or OH and Z is NH₂ or OH.

2. A compound according to claim 1 wherein Z is NH₂.

3. The compound of claim 2 which is 3-(p-carbamoylbenzyl)-7β-(D-α-phenylglycyl)amino-ceph-3-em-4-carboxylic acid or a pharmaceutically acceptable salt thereof.

4. The compound of claim 2 which is 3-(p-carbamolybenzyl)-7β-(D-α-p-hydroxyphenylglycyl)amino-ceph-3-em-4-carboxylic acid or a pharmaceutically acceptable salt thereof.

5. The compound of claim 1 which is 3-(m-carbamolybenzyl)-7β-(D-α-phenylglycyl)amino-ceph-3-em-4-carboxylic acid.

6. An antibacterial pharmaceutical composition in a form for administration to humans comprising an antibacterially effective amount of a compound of claim 1 and a conventional physiologically acceptable carrier.

7. An antibacterial pharmaceutical composition in a form for administration to humans comprising an antibacterially effective amount of a compound of claim 3 and a conventional physiologically acceptable carrier.

8. An antibacterial pharmaceutical composition in a form for administration to humans comprising an antibacterially effective amount of a compound of claim 4 and a conventional physiologically acceptable carrier.

9. An antibacterial pharmaceutically composition in a form for administration to humans comprising an anitbacterially effective amount of a compound of claim 3 and a conventional physiologically acceptable carrier.

10. An antibacterial pharmaceutical composition in a form for administration to humans comprising an antibacterially effective amount of a compound of claim 5 and a conventional physiologically acceptable carrier.

11. A method of treating bacterial infections in humans which comprises administering to a human in need thereof an antibacterially effective amount of a compound of the formula

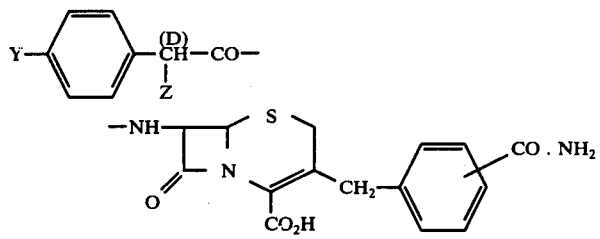

or a pharmaceutically acceptable salt thereof wherein Y is H or OH and Z is NH₂ or OH.

12. A method according to claim 11 wherein Z is NH₂.

13. A method according to claim 11 wherein the compound is 3-(p-carbamoylbenzyl)-7β-(D-α-phenylglycyl)amino-ceph-3-em-4-carboxylic acid or a pharmaceutically acceptable salt thereof.

14. A method according to claim 11 wherein the compound is 3-(p-carbamoylbenzyl)-7β-(D-α-p-hydroxyphenylglycyl)-amino-ceph-3-em-4-carboxylic acid or a pharmaceutically acceptable salt thereof.

15. A method according to claim 11 wherein the compound is 3-(m-carbamoylbenzyl)-7β-(D-α-phenylglycyl)amino-ceph-3-em-4-carboxylic acid or a pharmaceutically acceptable salt thereof.

* * * * *

UNITED STATES PATENT AND TRADEMARK OFFICE
CERTIFICATE OF CORRECTION

PATENT NO. : 4,060,611
DATED : November 29, 1977
INVENTOR(S) : Brian George James It is certified that error appears in the above-identified patent and that said Letters Patent are hereby corrected as shown below:

Claim 9, line 3, change "3" to -- 2 --.

Signed and Sealed this

Twelfth Day of September 1978

[SEAL]

Attest:

RUTH C. MASON
Attesting Officer

DONALD W. BANNER
Commissioner of Patents and Trademarks